United States Patent [19]

Nicolas et al.

[11] Patent Number: 6,121,491
[45] Date of Patent: Sep. 19, 2000

[54] PROCESS FOR THE PREPARATION OF (+/−) 3-(3,4-DICHLOROPHENYL)-2-DIMETHYLAMINO-2-METHYLPROPAN-1-OL OR CERICLAMINE (INN)

[75] Inventors: Marc Nicolas, Gaillac; Blandine Laboue, Angrie; Dominique Depernet, La Rochelle, all of France

[73] Assignee: Warner-Lambert Company, Morris Plains, N.J.

[21] Appl. No.: 09/381,118

[22] PCT Filed: Apr. 6, 1998

[86] PCT No.: PCT/EP98/02213

§ 371 Date: Dec. 20, 1999

§ 102(e) Date: Dec. 20, 1999

[87] PCT Pub. No.: WO98/45248

PCT Pub. Date: Oct. 15, 1998

[30] Foreign Application Priority Data

Apr. 7, 1997 [FR] France .................................. 97 04311

[51] Int. Cl.⁷ .................................................. C07C 229/00
[52] U.S. Cl. ........................... 564/393; 564/394; 560/38; 562/449
[58] Field of Search ..................... 564/393, 394; 560/38; 562/449

[56] References Cited

U.S. PATENT DOCUMENTS 4,536,342 8/1985 Oyama .
4,994,617 2/1991 Aubard .
5,472,970 12/1995 Calvet .

FOREIGN PATENT DOCUMENTS 0 138 156 A2 10/1984 European Pat. Off. .
0 237 366 A1 1/1987 European Pat. Off. .
0 569 276 A1 3/1993 European Pat. Off. .
2 378 746 8/1978 France .

OTHER PUBLICATIONS

Theodoridis, G., et al., *J. of Heterocyclic Chemistry*, "A New Approach to the Synthesis of Substituted 2(1H)–Quinolinones", 1991 vol. 28:849–852.
Patent Abstract of Japan, 1987 vol. 11:38, PCT International Search Report, PCT/EP98/02213.
Kaptain, B., et al., *J. of the Chem. Soc., Perkins Trans. 1*, "Chemo–Enzymatic Synthesis of (S)–(+)–Cericlamine . . . ", 1994, pp. 1495–1498.
Binovic, K., et al., *Chimie Therapeutique*, "Etude D'Une Nouvelle Serie De Derives Anorexigenes", 1968, vol. 3, pp. 313–320.

*Primary Examiner*—Samuel Barts
*Attorney, Agent, or Firm*—Charles W. Ashbrook

[57] ABSTRACT

Process for the preparation of cericlamine which consists: i) in arylating methacrylic acid with the diazonium chloride of 3,4-dichloroaniline, to obtain (+/−)2-chloro-3-(3,4-dichlorophenyl)-2-methylpropionic acid, ii) in aminating the acid with dimethylamine, to obtain (+/−)3-(3,4-dichlorophenyl)-2-dimethylamino-2-methylpropionic acid, or an alkaline metal salt thereof, iii) in esterifying the amino-acid or its salt, then, iv) in reducing the ester by a metal or organometal hydride to obtain (+/−)3-(3,4-dichlorophenyl)-2-dimethylamino-2-methyl-propan-1-ol.

7 Claims, No Drawings

PROCESS FOR THE PREPARATION OF (+/−) 3-(3,4-DICHLOROPHENYL)-2-DIMETHYLAMINO-2-METHYLPROPAN-1-OL OR CERICLAMINE (INN)

The application is a 371 of PCT/EP98/02213 filed Apr. 6, 1998.

The invention relates to a process for the preparation of cericlamine (INN), the intermediate synthesis compounds of the said process and their preparation.

Field of the Invention and Prior Art.

Cericlamine is (+/−)3-(3,4-dichlorophenyl)-2-dimethylamino-2-methylpropan-1-ol of formula (I)

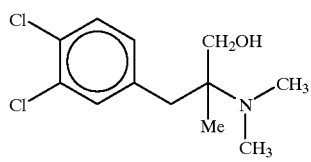

(I)

whose hydrochloride turns out to be an inhibitor of recapture of serotonin from the pharmacological point of view, and to show, in man, an anti-depressant activity.

The preparation of cericlamine is essentially described n the patent EP 237 366 published on Sep. 16, 1987 as well as the publication which appeared in J. CHEM. SOC. PERKIN TRANS.I, 1996 pp. 1495–1498. In these two documents, the pivotal precursor compound of cericlamine is 2-amino-3-(3,4-dichlorophenyl)-2-methylpropionic acid, which, similarly, is reduced in a first step by boron hydride to 2-amino-3-(3,4-dichlorophenyl)-2-methylpropan-1-ol, the compound, which, in a second step, is N,N-dimethylated by reaction with formaldehyde and formic acid as shown in scheme 1 which follows.

Scheme 1

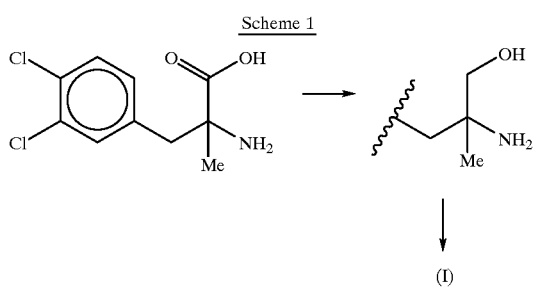

(I)

In its first step, this synthesis necessitates strong reducing agents and energetic conditions to efficiently reduce the carboxylic function. These conditions favour side reactions which result in sub-products, especially from dehalogenations, such as indicated in J. CHEM. SOC. PERKIN TRANS.I referred to above, products whose removal can only be to the detriment of the yield, and which, present in the state of traces in the final product, are considered as possibly toxic impurities from the pharmaceutical point of view.

As far as the preparation of 2-amino-3-(3,4-dichlorophenyl)-2-methylpropionic acid is concerned, a pivotal compound of these procedures:

the patent EP 237 366 indicates a preparation according to the process described in the patent FR 77 02360, which consists in alkylating an isocyano ester of formula $CH_3-CH-(NC)-COOR$ with a 3,4-dichlorobenzyl halide, then in subjecting the intermediate obtained to simultaneous hydrolysis of the isocyano and ester groups to respectively generate the amine and acid functions of the amino acid.

This synthesis appears to be adaptable with difficulty to industrial production because of the reagents concerned, whose commercial access is improbable, or which necessitates delicate preparations, especially as far as the preparation of the isocyano ester is concerned, the publication J. CHEM. SOC. PERKIN. TRANS.I, 1994, pp. 1495–1498 describes a synthesis starting from the amide of N-benzylidenealanine, which is alkylated by 3,4-dichlorobenzyl chloride to obtain an intermediate which is subjected to two successive hydrolyses, at first that of the Schiff base and then that of the amide function, to finally obtain the amino acid.

In the same way as the process of FR 77 02360, this synthesis has major disadvantages such as the necessity to prepare the amide of N-benzylidenealanine.

Alternative procedures can be envisaged to prepare this pivotal compound. Thus, starting from 1-(3,4-dichlorophenyl)propan-2-one, it is possible, either by Strecker reaction to obtain an aminonitrile which, hydrolysed, leads to the acid, or, and more particularly, by Bucherer-Bergs reaction to prepare 5-(3,4-dichlorobenzyl)-5-methylhydantoin which, hydrolysed in alkaline medium, likewise leads to the acid. This last method can easily be carried out by a minor adaptation of the procedure described in the patent EP 569 276. However, these syntheses are dependent on the obtainment of 1-(3,4-dichlorophenyl)-propan-2-one which, whatever the preparation envisaged, necessitates an economically penalizing multi-step synthesis such as that starting from 3,4-dichlorobenzaldehyde, such as described in Chimie Ther., 3, 1968, pp. 313–320.

For the purposes of development and of commercialization of cericlamine as a pharmaceutical active principle intended for the treatment of depression in man, there appears, in view of this prior art, to be a need to have an industrial preparation process which is reliable and of indisputable economic significance.

SUMMARY OF THE INVENTION

Breaking with the prior art which, whatever the process, calls on elaborate starting compounds themselves necessitating difficult and costly preparations, the present invention is directed at a process for the preparation of cericlamine by a novel route, only necessitating four synthesis steps starting from currently marketed reagents. In addition, the process leads to chemical intermediates which are still unpublished.

Thus, in its principal object, the invention aims at a novel process for the preparation of cericlamine, and, in a second aspect, aims at novel chemical compounds, which are intermediates for carrying out the said process.

Scheme 2

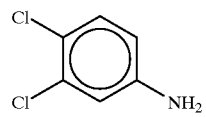

-continued

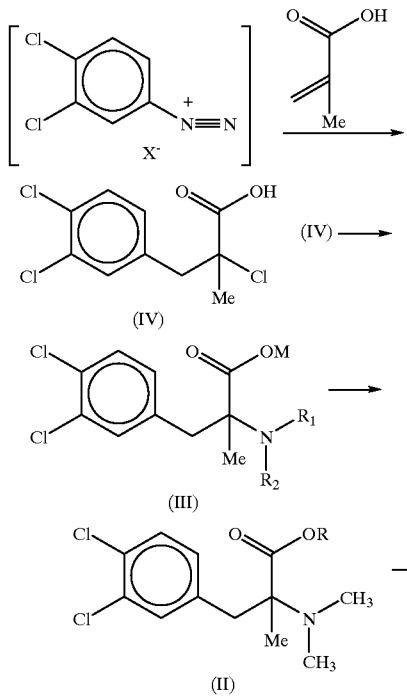

The principal object of the invention is directed, as shown in scheme 2 above, at a process for the preparation of ceriamine which consists:

i)—in arylating methacrylic acid with the diazonium chloride of 3,4-dichloroaniline, prepared in situ, to obtain (+/−)2-chloro-3-(3,4-dichlorophenyl)-2-methylpropionic acid (IV),

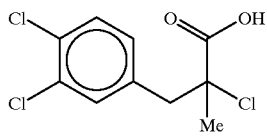

ii)—in aminating the acid (IV) with an amine $HNR_1R_2$ in which $R_1$ $R_2$ are hydrogen or methyl, to obtain an amino acid (III)

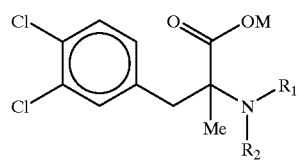

in which M is an alkali or alkaline earth metal or else hydrogen, $R_1$ $R_2$ being defined above, iii)—in esterifying an acid (III), then, when $R_1$ and/or $R2$ are hydrogen, in methylating the amine with formaldehyde and Formic acid to obtain an ester of (+/−)3-(3,4-dichlorophenyl)-2-dimethylamino-2-methylpropionic acid (II)

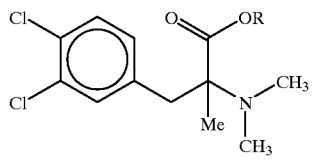

in which R is lower alkyl, iv)—in reducing the ester (II) by a metal or organometal hydride to obtain (+/−)3-(3,4-di-chlorophenyl)-2-dimethylamino-2-methylpropan-1-ol or ceriamine (INN) of formula (I) and in making the addition salt with hydrochloric acid.

In a second aspect, the invention is directed, by way of intermediate chemical compounds of the process, at the compounds of formula (V)

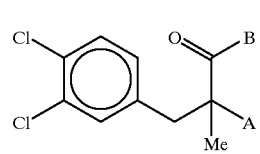

in which

A is a dimethylamino group or chlorine with the reservation that B is OH,

B is OM in which M is an alkali or alkaline earth metal or hydrogen, or else B is OR in which R is a lower alkyl radical.

DETAILED DESCRIPTION OF THE INVENTION

The process of the invention allows, as shown, ceriamine to be prepared in four steps starting from 3,4-dichloroaniline, which forms an incomparably advantageous synthesis with respect to those carried out until now.

More precisely as far as the process steps are concerned, the first, which consists in preparing the halo acid (IV) by arylation of methacrylic acid with a diazonium salt of 3,4-dichloroaniline (or 3,4-dichloro-benzenediazonium salt), is carried out according to the Meerwein reaction which is widely documented, especially in Org. React., 11, 189 (1960) & 24, 225–259 (1976). According to this reaction, G. Théodoridis et al. (J. Heterocyclic Chem., 28, 849 (1991)) prepare the methyl ester corresponding to the chlorinated intermediate (IV) of the process. This ester, involved in the process of the invention, turns out to be disappointing at the amination stage because of uncontrollable instability and/or reactivity which lead to mixtures of compounds which are unusable in the context of a process of industrial application.

As carried out in the invention, the Meerwein reaction consists in making the diazonium salt of 3,4-dichloroaniline in a first step in a conventional fashion with sodium nitrite in acid medium, and then, in a second stage, in situ, in carrying out the arylation of the methacrylic acid catalysed by a metallic halide chosen from the chlorides or bromides of cobalt, of manganese or alternatively of iron or of copper, which are preferred. When the catalyst is a bromide of $Cu^+$ or $C^{++}$, one obtains the brominated analogue of the acid (IV); more favourably, the diazotization is carried out in hydrochloric acid medium, then the arylation of the methacrylic acid is catalysed by $Fe^{++}$ chloride or a chloride of copper, $Cu^+$ being preferred, to obtain the 2-chloro-3-aryl-2-methylpropionic acid (IV).

Practically, the diazotization reaction takes place in acetone at a temperature lower than 10° C. using an excess of 3 to 5 and more favourably of 4 mol of acid with respect to 3,4-dichloroaniline and a quantity of 1 to 1.5 mol of sodium nitrite. The arylation which follows is carried out by reacting an excess of 1.25 to 2 mol and, more favourably, of 1.5 mol of methacrylic acid, the reaction being catalysed by the addition of 0.05 to 0.005 mol, and, preferably, of 0.02 mol of the chosen metallic halide.

The second step of the process relates to the amination of a halo acid and more particularly to that of the chloro acid (IV) by an amine $HNR_1R_2$ in which $R_1$ $R_2$ are hydrogen or methyl. This type of reaction is documented generally in the work "Advanced Organic Chemistry"—J. March—3rd Edition (ed. J. Wiley Intersciences) p. 364 & following, and consists, in the context of the invention, in the reaction of an amine chosen from ammonia, methylamine and dimethylamine with the intermediate (IV). For essentially practical reasons, ammonia and more particularly dimethylamine are preferred, it being possible for the reaction to be carried out in various solvents chosen from water, lower alcohols, halogenated hydrocarbons of low boiling point, aromatic hydrocarbons or alternatively aliphatic ketones or nitriles, including especially acetone and acetonitrile which are the preferred solvents.

Practically, carrying out the reaction consists in dissolving or dispersing the intermediate (IV) in the solvent or the solvent mixture chosen and, per 1 mol of (IV), in adding from 0.1 to 3 mol and, more advantageously, 1 mol of potash or, better, of soda in flakes and, optionally, from 0.01 to 0.2 mol of a so-called phase-transfer catalyst such as benzyltriethylammonium chloride. The amine considered is introduced into the mixture cooled to 0° C., either in liquefied form or by bubbling in gas, and in a quantity from 2 to 100 mol with respect to (IV). Favourably, from 30 to 70 mol in excess are used when ammonia is involved, and from 3 to 10 mol in excess when dimethylamine is used. For the latter, an alternative consists in introducing it in solid state in the form of its addition salt with an acid such as in the form of its hydrochloride, in which case the equimolar quantity of potash or of soda is added to the medium to displace, in situ, the dimethylamine from its salt.

The reaction is carried out, in a hermetically sealed reactor, with stirring at a temperature from 20 to 80° C. for 4 to 48 hours. Under favourable conditions, the reaction is completed by heating to 30 to 50° C. and, preferably, to 40° C., after 15 to 20 hours' contact. Following which the reactor is cooled to 10° C., the excess of amine is degassed by bubbling in an appropriate liquid which can be water or a lower alcohol, and then the reaction mixture is evaporated to obtain a residue comprising the alkali metal salt of the expected amino acid (III) in which $R_1$, $R_2$ correspond to the amine employed, the salt being either involved as it is in the following stage of the process if it is sufficiently pure, or treated to obtain the acid by displacement from its salt, which is carried out by dissolution of the residue in a minimum volume of water and then acidification of the solution to the isoelectric pH of the acid (III) with a strongly concentrated acid such as hydrochloric acid or sulphuric acid, a pH at which the insoluble acid (III) can be isolated. For practical reasons of industrial and economic nature, it is preferred, however, to involve directly the unisolated alkali metal salt in the stage which follows.

The third step of the process consists in esterifying the intermediate (III), in salt form or not in salt form, and then, optionally to N,N-dimethylate the amine when $R_1$ and/or $R_2$ are hydrogen. The possible esterification processes are varied, and a general review is found, for example, in the work "Advanced Organic Chemistry"—J. March—3rd Edition (ed. J. Wiley Intersciences) p. 348 & following. It is possible to use, among other things, the reactions with the lower primary alcohols such as methanol, ethanol, propanol or alternatively with a secondary alcohol such as isopropanol, by heating of the acid (III) with one of these alcohols and catalysts currently used such as concentrated sulphuric acid, paratoluenesulphonic acid or alternatively thionyl chloride or else alternatively to proceed by elimination of the water formed by the reaction with a dehydrating agent or alternatively by azeotropic distillation, these reactions leading to the amino esters (II) in which R is $C_1$ to $C_3$ lower alkyl.

Practically, it is preferred to carry out the alkylation of the acids (III) by alkylating reagents of formula W—(R)$_n$, in which n has a value of 1 or 2, R being methyl when n is 1 or 2, or, when n is 2, one of the two radicals R can optionally be hydrogen, the other being methyl, W is a radical of monovalent anionic type when n has a value of 1 and which is then a halogen such as, preferably, bromine, chlorine, or alternatively W is of divalent type when n is 2, such as a carbonate or a sulphate, the latter being particularly preferred.

The implementation of the process is an adaptation of the patent FR 71 08700 as far as the alkylation of the acids (III) by dimethyl sulphate is concerned. It consists in reacting in toluene for 1 mol of (III), in acid form or preferably in salt form, and in which $R_1$ $R_2$ are methyl, from 0.9 to 2.5 mol of dimethyl sulphate, and when $R_1$ and/or $R_2$ are hydrogen, in reacting (III) with 1.2 to 3.5 mol of dimethyl sulphate. It is preferred, when in (III) $R_1$ $R_2$ are methyl to use from 1.2 to 2.0 mot to obtain an amino ester (II) in which R, $R_1$ $R_2$ are methyl, and, when in (III) $R_1$ and/or $R_2$ are hydrogen to use from 1.4 to 2.8 mol of dimethyl sulphate. In this last case, a mixture of intermediate esters is obtained in which R is methyl, $R_1$ and/or $R_2$ are hydrogen or methyl, these compounds being subjected without isolation to a complementary N-methylation by a reaction of the Eschweiler-Clarke type with formaldehyde and formic acid. Practically, the working procedure of the reaction consists in dispersing the acid (III), preferably in the form of its sodium salt, in toluene, and then, at reflux of the solvent, in introducing dimethyl sulphate. The reaction medium is then maintained at reflux for 1 to 5 hours, then water is added and after alkaline extraction allowing the ester to be obtained in the toluene phase, in evaporating the solvent and obtaining the N,N-dimethylated amino ester (II). Optionally, the toluene phase is subjected to complementary methylation. For this, formaldehyde in aqueous solution and then pure formic acid are added to it. The mixture, with efficient stirring, is brought to reflux for 30 minutes to 3 hours, which allows the methylation to be completed and the dimethylamino ester (II) to be obtained.

As far as the reduction stage of the ester which follows is concerned, a general account will be found in "Advanced Organic Chemistry"—J. March—3rd Edition (ed. J. Wiley Intersciences) p. 1093 & following. The structure of the ester (II), and especially the presence of the chlorine disubstitution, prohibits the use of reducing agents and/or of violent conditions such as those of catalytic hydrogenation or of a so-called Bouveault and Blanc reaction. Thus, the best suited processes consist in the reduction of (II) with metallic or organometallic hydrides, which, for the monometallic hydrides, are of general formula $M_1(H)_{y1}(R_3)_{z1}$ in which $M_1$ is aluminium or boron $R_3$ is linear or branched chain $C_2$ to $C_4$ lower alkyl, y1 is 1, 2 or 3, z1 is 0, 1 or 2 the sum y1+z1 in any case being equal to 3, or else are hydrides derived from silicon such as the hydride of polymethylhydroxysiloxane whose action is catalysed by a metalloreducing agent complex such as described in the publication WO 96/12694. The dimetallic complex hydrides employed for the reduction of (II) are of formula $M_2M_1(H)_{y2}(R_3)_{z2}$ in which $M_1$ is aluminium or boron, $M_2$ is an alkali metal, especially lithium or sodium, $R_3$ is linear or branched chain $C_2$ to $C_4$ lower alkyl or else linear or branched chain $C_2$ to $C_4$ lower alkoxy or alternatively alkoxyalkoxy, y2 is 2, 3 or 4, z2 is 0, 1, 2 or 3 the sum y2+z2 in any case being equal to 4.

Among these hydrides, those which are dimetallic are preferred and, for those in which z2 is 0, those where $M_1$ is aluminium and $M_2$ is lithium or else those where $M_1$ is boron and $M_2$ sodium, namely, in the latter case, sodium borohydride which, favourably, is used in the presence of a Lewis acid such as $AlCl_3$ or in the presence of a strong acid such as sulphuric acid. As far as the hydrides in which z2 is 1, 2 or 3 are concerned, those are preferred in which z2 has the value 2, $M_2$ is sodium, $M_1$ is aluminium and $R_3$ is alkoxyalkoxy such as the methoxyethoxy group.

The hydride which is particularly preferred is lithium aluminium hydride (LAH) which is used in the form of its association complex with tetrahydrofuran (THF), a complex which is soluble in toluene which is the preferred reaction solvent. Thus, the procedure consists in a first step in preparing the LAH-THF complex in toluene by adding from 3 to 10 molar equivalents of THF to 1 mol of LAH, and then, the soluble complex being formed, in introducing from 1.5 to 2.0 mol of ester (II) and preferably from 1.65 to 1.75 mol of this ester per 1 mol of LAH employed. The reaction is carried out under a nitrogen atmosphere, keeping it from 30 minutes to 24 hours at a temperature of between 10 to 110° C. The preferred conditions for this reduction are from 1 to 3 hours from 60 to 110° C., following which the complexes are decomposed by water in alkaline medium and cericlamine (I) is isolated after filtration of the salts and evaporation of the solvents. The product, obtained in the crude state, is purified by crystallization in alkanes of boiling point of between 50 and 100° C. such as hexane, and then salified by hydrochloric acid according to conventional processes adapted to industry.

The entirety of the successive reactions particularly appropriate for the preparation, in four stages, of cericlamine starting from 3,4-dichloroaniline are:

i)—to carry out the diazotization of the 3,4-dichloroaniline in acetone in hydrochloric acid medium at a temperature lower than 10° C. using 4 mol of acid with respect to 3,4-dichloroaniline and from 1 to 1.5 mol of sodium nitrite, then to react 1.5 mol of methacrylic acid, the arylation being catalysed by 0.02 mol of copper chloride, to obtain the chlorinated acid intermediate (IV), then ii)—to aminate the intermediate (IV) with ammonia or, preferably, dimethylamine, in acetone or, preferably, acetonitrile, by dissolving or dispersing (IV) in the solvent and, per 1 mol, to add 1 mol of soda in flakes, then
to introduce at a temperature of approximately 0° C., either from 30 to 70 mol of ammonia or, in a preferred manner, from 3 to 10 mol of dimethylamine, then to heat the mixture with stirring and under pressure from 30 to 50° C. and preferably to 40° C. for 15 to 20 hours, then to evaporate the reaction mixture to obtain the sodium salt of the amino acid (III) in which $R_1$, $R_2$ are hydrogen if amination with ammonia and are, preferably, methyl, if amination with dimethylamine, then iii)—to methylate the sodium salt of an amino acid (III) by reacting, at reflux, toluene with 1 mol of the acid salt (III) in which $R_1$ $R_2$ are methyl, from 1.2 to 2.0 mol of dimethyl sulphate to obtain the ester (II) in which R, $R_1$ and $R_2$ are methyl and, when in (III) $R_1$ $R_2$ are hydrogen, to react from 1.4 to 2.8 mol of dimethyl sulphate, and then without isolation, to N-methylate the mixture of esters obtained, in which R is methyl, $R_1$ and/or $R_2$ are hydrogen or methyl, with formaldehyde and formic acid to obtain the ester (II), and then iv)—to reduce the ester (II) with lithium aluminium hydride (LAH) in the form of an association complex with tetrahydrofuran (THF), in toluene and under a nitrogen atmosphere, which consists in adding from 3 to 10 molar equivalents of THF to 1 mol of LAH, then to introduce from 1.65 to 1.75 mol of the ester (II) and then to allow reduction to take place for 1 to 3 hours at a temperature from 60 to 110° C., then to decompose the complexes with water in alkaline medium and, after evaporation of the solvents, to obtain cericlamine (I) which is purified by crystallization from hexane and then salified with hydrochloric acid according to processes adapted for industry.

In addition, as novel chemical compounds of formula (V), which are intermediates of the process, the invention is directed particularly at:

(+/−)2-chloro-3-(3,4-dichlorophenyl)-2-methyl-propionic acid, (+/−)3-(3,4-dichlorophenyl)-2-dimethylamino-2-methyl-propionic acid and its sodium salt, methyl (+/−)3-(3,4-dichlorophenyl)-2-dimethylamino-2-methylpropionate.

The experimental section which follows, illustrates, without limiting it, the preferred process for the preparation of cericlamine starting from 3,4-dichloroaniline and methacrylic acid.

EXPERIMENTAL SECTION

General points—in the description of the examples which follow:

drying of the solvents is understood as meaning that anhydrous $MgSO_4$ is added in sufficient quantity then this product is separated by filtration, distillation or removal by distillation of the solvents is understood as meaning that its operations are carried out under a vacuum of 25 to 50 mm of Hg, the melting points reported are not corrected and are determined by differential thermal analysis (Mettler apparatus, type 20 oven, TC11 programmer), the chromatographic purity is determined on thin layers (TLC) of silica (supplier Merck), the qualitative and proportional composition of the elution mixtures being indicated, the proton magnetic resonance spectra are carried out on a Varian EM 360 apparatus (60 MHz), the compounds being dissolved in deuterochloroform or deuterated dimethyl sulphoxide, T.M.S being used as internal reference. The spectra are reported in the examples by the shift of the signals in ppm with respect to TMS, their appearance and the number of protons which they represent.

Example 1. (preferred)

i)—preparation of (+/−)2-chloro-3-(3,4-dichlorophenyl)-2-methylpropionic acid—[(IV), compound (V) for A=Cl, B=OH]

In a reactor, 60.0 g (0.37 mol) of 3,4-dichloroaniline are dissolved in 300 ml of acetone. Without exceeding 20° C., 125 ml of 36% HCl are added in 10 min. The mixture is cooled to 0° C. and, under a nitrogen atmosphere, a solution of 27.7 g (0.39 mol) of 97% sodium nitrite in 74 ml of water are added to it in 15 min and keeping between 0 and 5° C. 47.8 9 (0.56 mol) of methacrylic acid and 104 ml of pure acetic acid are then added successively and then, between 3 and 5° C., a solution of 0.76 9 (7.4 mmol) of cuprous chloride in 24 ml of 10% HCl. This introduction is exothermic and is accompanied by evolution of nitrogen. The mixture is then kept for 2 h with stirring to reach 20° C. and then 74 ml of water are added.

The lower organic phase is drawn off and the aqueous phase is extracted 2 times with 200 ml of toluene. 740 ml of water are added to the combined organic phases and 150 ml of 30% NaOH solution are added at t<25° C. The alkaline phase is separated and the toluene phase is extracted with 200 ml of water.

The combined alkaline aqueous phases are acidified at t<25° C. with 60 ml of 93% $H_2SO_4$ and the mixture is extracted with 750 ml of toluene. The acid phase is separated, extracted with 350 ml of toluene and then the combined organic phases are dried and the solvent is removed by distillation. The residue (106 g) is taken up with 110 ml of hexane at 50° C. approximately and then the solution is cooled with stirring to 0° C. The insoluble matter is filtered, washed 2 times with 30 ml of hexane at 0° C. and then dried in vacuo at 40° C. to constant weight. Weight: 80.2 g-yield=80.9%-m.p.=105.2° C.

TLC: Rf=0.10 to 0.40 (hexane-acetone v/v); $H^1$ NMR δ ppm; 1.7 (s, 3H); 3.25 (s, 2H); 7.2 (m, 3H); 9.7 (s, 1H).

ii)—preparation of (+/−)3-(3,4-dichlorophenyl)-2-dimethylamino-2-methylpropionic acid and of its sodium salt—[(III) M=H or Na, compound (V) for A=dimethylamino, B=OM]

50.0 ml of acetonitrile into which 10.0 g (220 mmol) of dimethylamine have previously been introduced in the cold are introduced into a constant volume reactor, and then 1.5 9 (37.5 mmol) of NaOH in flakes and 10.0 g of the chloro acid obtained in the previous stage are added. The reactor is closed and then heated with stirring to 40° C. for 17 h in the course of which the pressure first rises and then decreases in the course of the progress of the reaction. The reactor is cooled to 10° C. approximately, then opened and the mixture is distilled in vacuo. 50 ml of toluene are added to the residue, which are removed and the residue is taken up again with stirring with 30 ml of toluene. The insoluble sodium (+/−)3-(3,4-dichlorophenyl)-2-dimethylamino-2-methylpropionate is filtered and dried in vacuo. Weight: 8.6 g-yield=76.9%-m.p.=255–260° C.

TLC: Rf=0.20 to 0.30 (chloroform-methanol-toluene-conc. ammonia 30/20/20/1.5 v/v); $H^1$ NMR δ ppm; 1.4 (s, 3H); 2.85 (s, 6H); 3.1 (s, 2H); 7.3 (m, 3H).

The acid is obtained by dissolution of 7.5 g (25 mmol) of the sodium salt in 40 ml of water and then acidification to pH 6.5–6.6 with 36% HCl. The suspension is kept with stirring at 5° C. for 2 h and then the acid (III) is filtered and dried in vacuo. Weight: 6.6 g-yield=95%-m.p.=250° C. $H^1$ NMR δ ppm; 1.45 (s, 3H); 3.0 (s, 6H); 3.2 (s, 2H); 7.4 (m, 3H); 9.75 (s, 1H).

iii)—preparation of methyl (+/−)3-(3,4-dichlorophenyl)-2-dimethylamino-2-methylpropionate [(II), R=CH_3; compound (V) for A=dimethylamino, B=OR]

7.0 9 (23 mmol) of the sodium salt obtained in the previous stage in 21.0 ml of toluene are introduced into a reactor. The suspension is heated to reflux and 4.2 g (33 mmol) of dimethyl sulphate are then added in 15 min. The appearance of the medium changes and two phases are obtained; it is kept at reflux for 2 h, cooled to 70° C., 10 ml of water are added and the mixture is stirred for 12 h at 20–25° C.

The aqueous phase is then separated and the toluene phase is extracted 2 times with 10 ml of water. The combined aqueous phases are rendered alkaline at t<25° C. with 6 ml of 30% soda lye and then are extracted with 30 ml of toluene. The organic phase is separated, the aqueous phase is extracted 2 times with 10 ml of toluene and the combined organic phases are washed with 10 ml of water.

The toluene is removed by distillation and the compound (II) is obtained crude in the form of a pale yellow viscous oil in a state of purity which is satisfactory to be employed in the reduction stage which follows.

Weight: 4.3 g-yield=63.2% TLC: Rf=0.75 (chloroform-methanol-toluene-conc. ammonia 30-30-30-1.5 v/v); $H^1$ NMR δ ppm; 1.2 (t, 3H); 2.4 (s, 6H); 3.1 (q, 2H); 3.75 (s, 3H); 7.3 (m, 3H).

iv)—preparation of (+/−)3-(3,4-dichlorophenyl)-2-dimethylamino-2-methylpropan-1-ol (I) or cericlamine (INN)

0.35 g (8.74 mmol) of lithium aluminium hydride as a powder in 8.5 ml of perfectly dry toluene are introduced into a dry reactor, protected from moisture and under a nitrogen atmosphere. 1.4 ml of dry tetrahydrofuran are then added dropwise to the suspension. The addition is slightly exothermic and a solution of 4.3 g (15 mmol) of the dimethylamino ester prepared in the previous stage iii) in 4.3 ml of toluene is then added. This addition is likewise exothermic and the temperature rises from 23 to 32° C.

The mixture, with stirring, is then kept for 2 h 30 at 20° C., then heated for 1 h 30 to 60° C. and then again for 1 h to reflux of the toluene before being left for 16 h. 0.33 ml of water is then added dropwise at t<18° C. then a solution of 0.06 g of NaOH flakes in 0.33 ml of water, and then 1.00 ml of water. The suspension is stirred for 30 min. The insoluble matter is filtered, taken up in two successive repetitions with 15.5 ml of toluene and filtered.

The combined toluene phases are evaporated and the residue is dissolved at reflux in 16 ml of hexane and, by cooling, a crystallization is apparent towards 40° C. After cooling to 20° C. the suspension is kept for 2 h at t<5° C. The insoluble matter is filtered, washed with cold hexane and then dried at 50° C. in vacuo to constant weight.

Weight: 3.40 g-yield=87.8%-m.p.=86.3° C. TLC: Rf=0.10–0.40 (ethanol-hexane-chloroform v/v/v); $H^1$ NMR δ ppm; 0.8 (s, 3H); 2.05 (s, 1H); 2.4 (s, 6H); 2.75 (s, 2H); 3.3 (s, 2H); 7.3 (m, 3H).

hydrochloride: 2.0 g (7.63 mmol) of the compound (I) obtained are dissolved at 40° C. in 5.2 ml of dry ethanol. After cooling to 30° C. 2.5 g of 11.8% (w/v) hydrochloric ethanol (8.01 mmol) are added and then the solution is heated to 50° C. and 8.0 ml of diisopropyl ether are added. The solution is cooled with stirring, a crystallization takes place at 35° C. and the mixture is kept for 2 h at this temperature and then cooled to 10° C. After 2 h the insoluble matter is filtered, washed and dried in vacuo to constant weight. Weight: 1.9 g-yield=83.3%-m.p.=173.3° C.

TLC: Rf=0.40–0.60 (chloroform-ethanol-hexane-conc. ammonia 30-30-30-1.5 v/v).

Example 2 i)—(+/−)2-chloro-3-(3,4-dichlorophenyl)-2-methylpropionic acid—[(IV), prepared as described in i) of Example 1 above.

ii)—preparation of sodium (+/−)2-amino-3-(3,4-dichlorophenyl)-2-methylpropionate—[(III) M=Na, R=R₂=H]

The reaction is carried out according to the working procedure described in ii) of Example 1 starting with 10.0 g (0.037 mol) of chloro acid (IV) and 35.0 g (2.06 mol) of ammonia. After treatments, the sodium salt of the product is obtained. Weight: 8.3 g-yield=82.2%-m.p.=275–280° C.

TLC: Rf=0.30–0.40 (chloroform-ethanol-hexane-conc. ammonia 30-30-30-1.5 v/v); $H^1$ NMR δ ppm; 1.35 (s, 3H); 2.1 (s, 2H); 3.0 (q, 2H); 7.4 (m, 3H).

iii)—Preparation of methyl (+/−)3-(3,4-dichlorophenyl)-2-dimethylamino-2-methylpropionate [(II), R=CH₃; compound (V) for A=dimethylamino, B=OR]

iii.a) 7.0 9 (26 mmol) of the acid sodium salt obtained above in 21 ml of dry toluene are introduced into a reactor. The suspension is brought to reflux with stirring and 4.6 9 (36 mmol) of dimethyl sulphate are added dropwise. The mixture is kept at reflux for 2 h and then cooled to 40° C. and 10 ml of water are added and then the mixture is cooled to 20° C. The mixture is kept for 15 min with stirring and then left for 16 h. The aqueous phase is separated and the toluene phase is extracted 2 times with 6 ml of water. The combined aqueous phases are rendered alkaline at t<25° C. with 4.2 ml of 30% soda lye and then are extracted with 20 ml of toluene. The organic phase is separated and the aqueous phase is extracted 2 times with 5 ml of toluene and then the combined organic phases are washed with 6 ml of water.

iii.b) 7.8 g (78 mmol) of 30% formaldehyde solution are added in a reactor to the toluene phases obtained. The mixture is brought to reflux with stirring and then 5.8 9 (101 mmol) of 80% formic acid are added keeping the temperature at 85–90° C.

The mixture is heated with stirring at 85–90° C. for 1 h 30 and, after cooling to 35° C., 8.4 ml of 30% soda lye are added at t<35° C. The organic phase is separated and the aqueous phase extracted 2 times with 8 ml of toluene, and then the combined toluene phases are washed 3 times with 6 ml of water and the toluene is removed by distillation. The dimethylamino ester (II) is obtained crude in a TLC state of purity sufficient to be employed as it is in the final reduction stage.

Weight: 4.3 g-yield=57.2%; TLC: Rf=0.40–0.60 (dichloromethane-acetone 85-15 v/v); $H^1$ NMR: Identical to the compound obtained in iii) of Example 1 iv)—Preparation of (+/−)3-(3.4-dichlorophenyl)-2-dimethylamino-2-methylpropan-1-ol (I) or cericlamine (INN), the product is prepared as described in iv) of Example 1.

What is claimed is:

1. Process for the preparation of (+/−)3-(3,4-dichlorophenyl)-2-dimethylamino-2-methylpropan-1-ol (I) or cericlamine which consists:

i)—in arylating methacrylic acid with the diazonium chloride of 3,4-dichloroaniline, prepared in situ, to obtain (+/−)2-chloro-3-(3,4-dichlorophenyl)-2-methylpropionic acid (IV),

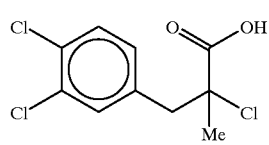

(IV)

ii)—in aminating the acid (IV) with an amine $HNR_1R_2$ in which $R_1$ and $R_2$ are independently hydrogen or methyl, to obtain an amino acid (III)

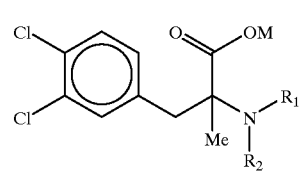

(III)

in which M is an alkali or alkaline earth metal or else hydrogen, $R_1$ and $R_2$ being as defined above, then iii)—in esterifying an acid (III), then, when $R_1$ and/or $R_2$ are hydrogen, in methylating the amine with formaldehyde and formic acid to obtain a (+/−)3-(3,4-dichlorophenyl)-2-dimethyl-amino-2-methylpropionic acid ester(II)

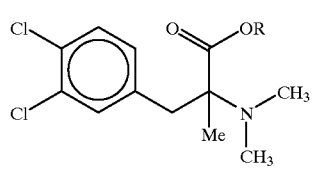

(II)

in which R is lower alkyl, then iv)—in reducing the ester (II) by a metal or organometal hydride to obtain (+/−)3-( 3,4-dichlorophenyl)-2-dimethylamino-2-methylpropan-1-ol or cericlamine (INN) of formula (I)

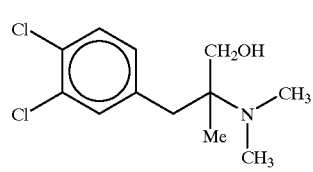

(I)

and in making the addition salt with hydrochloric acid.

2. Process according to claim 1, in which the diazonium chloride of 3,4-dichloroaniline is employed at a rate of 1 mol for the arylation with 1.5 mol of methacrylic acid in the presence of 0.02 mol of cuprous chloride to obtain the acid (IV).

3. Process according to claim 1 or 2 in which 1 mol of acid (IV) is aminated in acetonitrile by heating under pressure at 40° C. for 15 to 20 hours with 1 mol of soda and from 3 to 10 mol of dimethylamine to obtain the amino acid (III) in which M is sodium, $R_1$ and $R_2$ are both methyl.

4. Process according to claim 1 or 3 in which 1 mol of amino acid (III) is esterified in toluene with 1.4 to 2.8 mol of dimethyl sulphate and then N-methylated with formaldehyde and formic acid when in (III) $R_1$ and $R_2$ are hydrogen, and with 1.2 to 2.0 mol of dimethyl sulphate when in (III) $R_1$ and $R_2$ are methyl, to obtain the amino ester (II) in which R, $R_1$ and $R_2$ are methyl.

5. Process according to claim 1 or 4 in which 1.65 to 1.75 mol of amino ester (II) are reduced in toluene with a lithium aluminium hydride-tetrahydrofuran addition complex prepared starting from 1 mol of hydride, to obtain (+/−)3-(3, 4-dichlorophenyl)-2-dimethylamino-2-methylpropan-1-ol (I) or cericlamine which is optionally salified with hydrochloric acid.

6. Process according to claim 1 in which:

the diazonium chloride of 3,4-dichloroaniline is employed at a rate of 1 mol for the arylation with 1.5 mol of methacrylic acid in the presence of 0.02 mol of cuprous chloride to obtain the acid (IV), 1 mol of acid (IV) is aminated in acetonitrile by heating under pressure at 40° C. for 15 to 20 hours with 1 mol of soda and from 3 to 10 mol of dimethylamine to obtain the amino acid (III) in which M is sodium, $R_1$ and $R_2$ are both methyl, 1 mol of amino acid (III) is esterified in toluene with 1.4 to 2.8 mol of dimethyl sulphate and then N-methylated with formaldehyde and formic acid when in (III) $R_1$ and $R_2$ are hydrogen, and with 1.2 to 2.0 mol of dimethyl sulphate when in (III) $R_1$ and $R_2$ are methyl, to obtain the amino ester (II) in which R, $R_1$ and $R_2$ are methyl, 1.65 to 1.75 mol of amino ester (II) are reduced in toluene with a lithium aluminium hydride-tetrahydrofuran addition complex prepared starting from 1 mol of hydride, to obtain (+/−)3-(3,4-dichlorophenyl)-2-dimethylamino-2-methylpropan-1-ol (I) or cericlamine which is optionally salified with hydrochloric acid.

7. As novel chemical compounds, which are intermediates of the process, the compounds of formula (V)

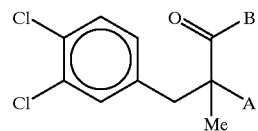

(V)

in which

A is a dimethylamino group or chlorine with the reservation that B is OH,

B is OM in which M is an alkali or alkaline earth metal or hydrogen, or else B is OR in which R is a lower alkyl radical, and which are:

(+/−)2-chloro-3-(3,4-dichlorophenyl)-2-methylpropionic acid, (+/−)3-(3,4-dichlorophenyl)-2-dimethylamino-2-methylpropionic acid and its sodium salt, methyl (+/−)3-(3,4-dichlorophenyl)-2-dimethylamino-2-methylpropionate.

\* \* \* \* \*